(12) United States Patent
Malawey et al.

(10) Patent No.: US 7,970,175 B2
(45) Date of Patent: Jun. 28, 2011

(54) METHOD AND APPARATUS FOR ASSESSING HEAD POSE OF A VEHICLE DRIVER

(75) Inventors: Phillip V. Malawey, Kokomo, IN (US); Matthew R. Smith, Westfield, IN (US); Gerald J. Witt, Carmel, IN (US)

(73) Assignee: Delphi Technologies, Inc., Troy, MI (US)

( * ) Notice: Subject to any disclaimer, the term of this patent is extended or adjusted under 35 U.S.C. 154(b) by 1093 days.

(21) Appl. No.: 11/796,807

(22) Filed: Apr. 30, 2007

(65) Prior Publication Data

US 2008/0266552 A1    Oct. 30, 2008

(51) Int. Cl.
G06K 9/00 (2006.01)
G06K 9/20 (2006.01)
B60Q 1/00 (2006.01)
G08B 23/00 (2006.01)
B60K 28/00 (2006.01)

(52) U.S. Cl. ........ 382/103; 382/104; 382/106; 382/107; 382/321; 340/438; 340/526; 340/529; 340/575; 340/576; 180/272

(58) Field of Classification Search .................. 382/103, 382/104, 106, 107, 321; 340/438, 526, 529, 340/575, 576; 180/272

See application file for complete search history.

(56) References Cited

U.S. PATENT DOCUMENTS

| | | | | |
|---|---|---|---|---|
| 3,903,514 A * | 9/1975 | Mazzola | | 340/575 |
| 4,625,329 A | 11/1986 | Ishikawa et al. | | |
| 5,322,245 A * | 6/1994 | Bassick | | 244/122 B |
| 6,154,559 A * | 11/2000 | Beardsley | | 382/103 |
| 6,184,791 B1 * | 2/2001 | Baugh | | 340/576 |
| 6,575,902 B1 * | 6/2003 | Burton | | 600/300 |
| 6,942,248 B2 * | 9/2005 | Breed et al. | | 280/735 |
| 7,098,812 B2 * | 8/2006 | Hirota | | 340/439 |
| 7,596,242 B2 * | 9/2009 | Breed et al. | | 382/103 |
| 2003/0228036 A1 * | 12/2003 | Paviot et al. | | 382/115 |
| 2005/0131607 A1 | 6/2005 | Breed | | |
| 2006/0042851 A1 * | 3/2006 | Herrmann et al. | | 180/271 |

FOREIGN PATENT DOCUMENTS

WO    97/11862    4/1997

OTHER PUBLICATIONS

Pappu, et al. "A Qualitative Approach to Classifying Gaze Direction." Automatic Face and Gesture Recognition, 1998. Proceedings. Third IEEE International Conference on . (1998): 160-165. Print.*
European Search Report dated August 8, 2008.

* cited by examiner

Primary Examiner — Matthew C Bella
Assistant Examiner — Michael A Newman
(74) Attorney, Agent, or Firm — Thomas N. Twomey

(57) ABSTRACT

The head pose of a motor vehicle driver with respect to a vehicle frame of reference is assessed with a relative motion sensor positioned rearward of the driver's head, such as in or on the headrest of the driver's seat. The relative motion sensor detects changes in the position of the driver's head, and the detected changes are used to determine the driver's head pose, and specifically, whether the head pose is forward-looking (i.e., with the driver paying attention to the forward field-of-view) or non-forward-looking. The determined head pose is assumed to be initially forward-looking, and is thereafter biased toward forward-looking whenever driver behavior characteristic of a forward-looking head pose is recognized.

3 Claims, 5 Drawing Sheets

METHOD AND APPARATUS FOR ASSESSING HEAD POSE OF A VEHICLE DRIVER

TECHNICAL FIELD

The present invention relates to driver distraction monitoring in motor vehicles, and more particularly to a method and apparatus for assessing the head pose of a driver.

BACKGROUND OF THE INVENTION

Each year numerous automobile accidents are caused by driver distractions, and many of the distractions are visual in nature. For this reason, there has been interest in developing a driver monitoring system for determining if the driver is paying attention to the forward field-of-view. This information can be used to issue an alert if the driver's attention is directed away from the road too long or too often, and possibly to belay other warnings (such as collision-avoidance warnings) if the driver is paying attention to the forward field-of-view. An example of such a monitoring system is Delphi Corporation's Driver State Monitor, which processes a video image of the driver's face to detect and track the driver's eyes for assessing eye gaze. However, detection of facial features such as eyes can be hampered by various kinds of obstructions (including sunglasses) disposed between the video imager and the driver's face. Moreover, the distance between the video imager and the driver's face can vary considerably from driver to driver, and it can be difficult to provide adequate controlled illumination of the driver's face. While these drawbacks can be satisfactorily addressed to a large extent by sophisticated processing of the video data, the system cost is frequently too high for most production vehicles due to the combined cost of the imager, optics and signal processor. Accordingly, what is needed is a more cost-effective and yet reliable way of assessing driver head pose.

SUMMARY OF THE INVENTION

The present invention is directed to an improved method and apparatus for assessing the head pose of a vehicle driver with respect to a vehicle frame of reference based on a relative motion sensor positioned rearward of the driver's head, such as in or on the headrest of the driver's seat. The relative motion sensor detects changes in the position of the driver's head, and the detected changes are used to track the driver's head pose and to determine whether the head pose is forward-looking (i.e., with the driver paying attention to the forward field-of-view) or non-forward-looking. The determined head pose is assumed to be initially forward-looking, and is thereafter biased toward forward-looking whenever driver behaviors characteristic of a forward-looking head pose are recognized.

BRIEF DESCRIPTION OF THE DRAWINGS

FIG. 1A depicts a driver of small stature, FIG. 1B depicts a driver of medium stature, and FIG. 1C depicts a driver of large stature.

FIG. 3A depicts the lateral output for a nominal forward-looking head pose, FIG. 3B depicts the lateral output for a momentary leftward glance, and FIG. 3C depicts the lateral output for a momentary rightward glance.

DESCRIPTION OF THE PREFERRED EMBODIMENT

The present invention is disclosed herein in the context of a driver distraction system that determines if the driver's attention is forward or non-forward relative to the forward direction of vehicle motion. However, the invention can additionally or alternatively be used to assess whether the driver is looking at an outside or rear view mirror, or a display or control panel for an accessory device such as an audio system or a navigation system, as mentioned below.

Fundamentally, the invention is directed to a system and method for assessing driver head pose with an optical sensor positioned rearward of the driver's head, such as in or on the headrest of the driver's seat. This diagrammatically depicted in FIGS. 1A-1C and 2.

Figures 1A, 1B, 1C:
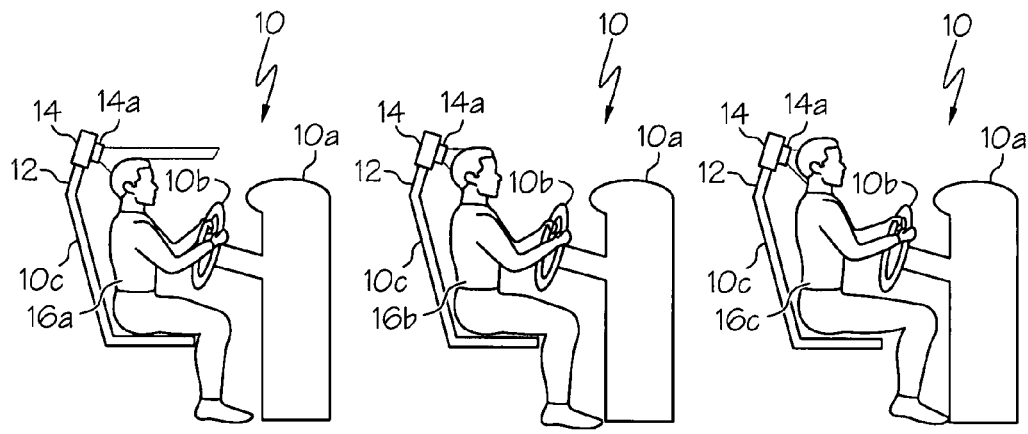
FIGS. 1A, 1B and 1C diagrammatically depict a vehicle passenger compartment with three different drivers occupying a seat equipped with an optical head pose sensing system according to this invention.

Referring to FIGS. 1A-1C, the reference numeral 10 generally designates a motor vehicle, specifically a motor vehicle passenger compartment. The passenger compartment 10 includes an instrument panel 10a, a steering wheel 10b and a driver seat 10c. The driver seat 10c is equipped with a fixed or adjustable headrest 12, and an optical sensor apparatus 14 is attached to the headrest 12. The optical sensor apparatus 14 includes a lens 14a for increasing the viewing angle of the internal optical sensor, and FIGS. 1A, 1B and 1C demonstrate that the viewing angle can be sufficiently wide to sense driver head movement with a small stature driver 16a, a medium stature driver 16b or a large stature driver 16c. FIGS. 1A-1C also demonstrate that the spatial relationship between the driver 16a/16b/16c and the optical sensor apparatus 14 is unaffected by seat position (up/down, fore/aft, etc.) since the optical sensor apparatus 14 moves with the seat 10c. This means that the scale of the image produced by the optical sensor will remain substantially the same for different drivers, and the optical sensor apparatus 14 will have no difficulty adequately illuminating the posterior portion of the driver's head under varying conditions that might be encountered.

Figure 2:
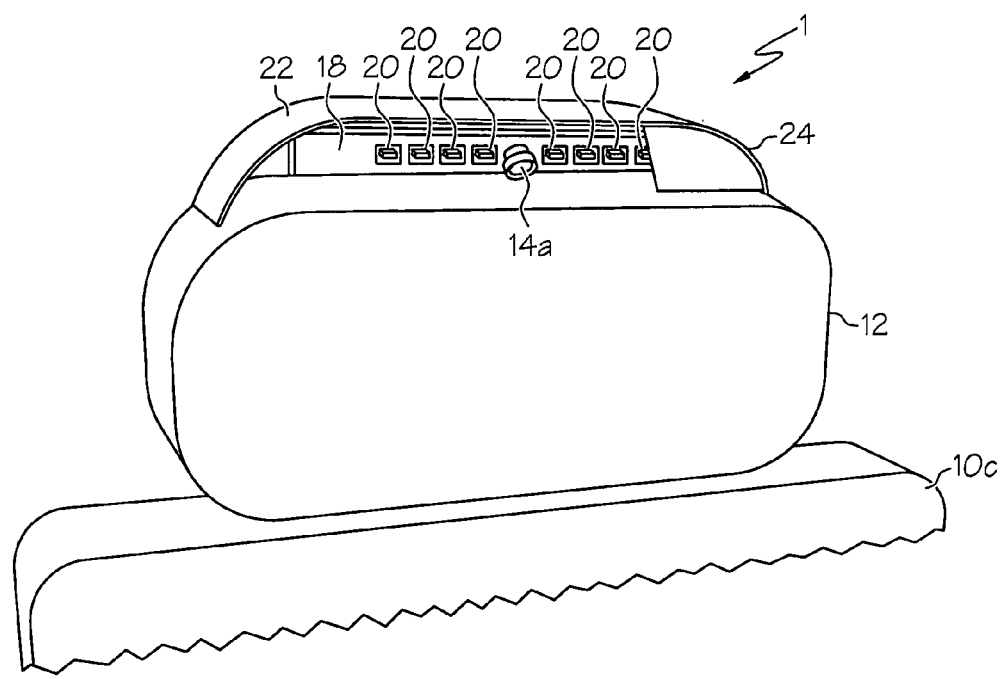
FIG. 2 is an isometric diagram of a mechanization of the optical head pose sensor of the present invention.

FIG. 2 illustrates a preferred and conceptual mechanization of the optical sensor apparatus 14. The optical and electronic components of the apparatus 14 are mounted in a housing affixed to the top of the headrest 12. The housing includes a mounting plate 18 through which the lens 14a and a plurality of infrared light emitting diode (LED) illuminators 20 protrude, a shroud 22 for shielding the optical sensor from stray ambient light, and a light-transmissive bezel 24 (only a portion of which is depicted in FIG. 2) for covering and protecting the lens 14a and illuminators 20. The illuminators 20 adequately illuminate the posterior portion of the driver's head for optimal performance of the optical sensor even during night driving. Of course, the number of illuminators 20 and their intensity may vary depending on sensor sensitivity and other factors. Also, it is possible to use more than one optical sensor and lens 14a, although doing so could significantly increase system cost.

As explained below, the optical sensor of the apparatus 14 is a relative motion sensor similar to the sensor used in an optical mouse for a personal computer. Sensors of this type are produced and sold by Agilent Technologies, Inc., for example, and include an imager chip and a digital signal processor programmed to recognize movement of imaged patterns and output Cartesian position coordinates based on the detected movement. The required data acquisition rate of the sensor depends on the application, and we have found that a standard data acquisition rate such as 30 frames/second is sufficient to detect driver head movement. Moreover, the sensor does not require high resolution or complicated signal processing for detecting and tracking specific facial features such as the driver's eyes, and is therefore considerably less expensive than optical sensors and processors ordinarily used for eye gaze detection. However, the sensor only provides the relative position or pose of the driver's head, as opposed to the absolute position or pose. In other words, the initial position of the driver's head is unknown.

Figure 3A:
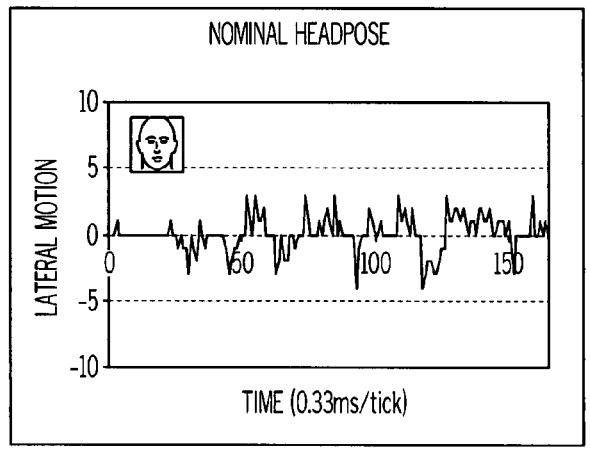
FIGS. 3A-3C graphically depict a lateral (i.e., horizontal) output of the optical head pose sensor of FIG. 2 in response to different driver head poses and movements.
Figure 3B:
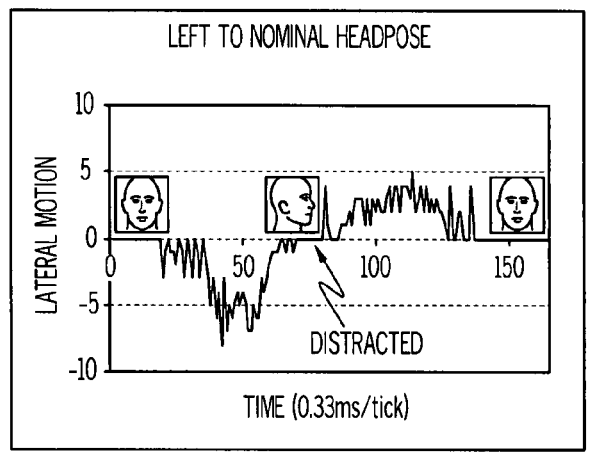
Figure 3C:
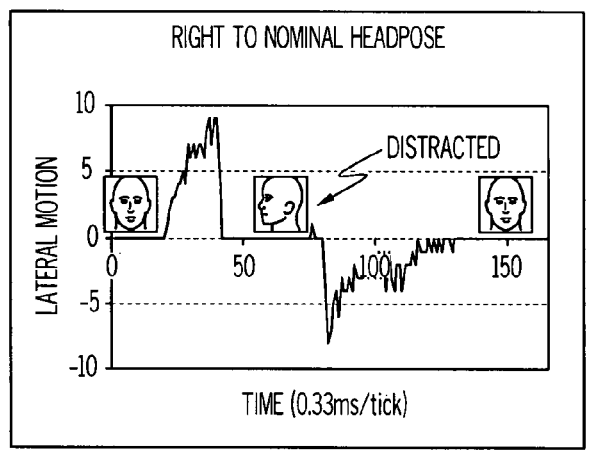

As applied to the apparatus 14, the relative motion optical sensor detects changes in the position of the driver's head with respect to the headrest 12, and outputs Cartesian coordinates corresponding to the current head pose, in relative terms. FIGS. 3A-3C graphically illustrate the detected lateral head motion (i.e., velocity) of a driver based on frame-to-frame changes in the lateral or X-coordinate output of the sensor. FIG. 3A depicts lateral coordinate data developed during vehicle operation when the driver's head pose is generally forward-looking. Referring to FIG. 3A, the detected movement may be due to vibration or small head movements, and the data is somewhat erratic with alternating leftward and rightward movements. FIG. 3B depicts lateral coordinate data developed during vehicle operation when the driver momentarily glances to the left at an outside mirror mounted on the driver-side door. FIG. 3C depicts lateral coordinate data developed during vehicle operation when the driver momentarily glances to the right at an outside mirror mounted on the passenger-side door. The detected movements shown in FIGS. 3B and 3C are decidedly non-random and clearly distinguishable from the forward-looking movements of FIG. 3A.

Figure 4:
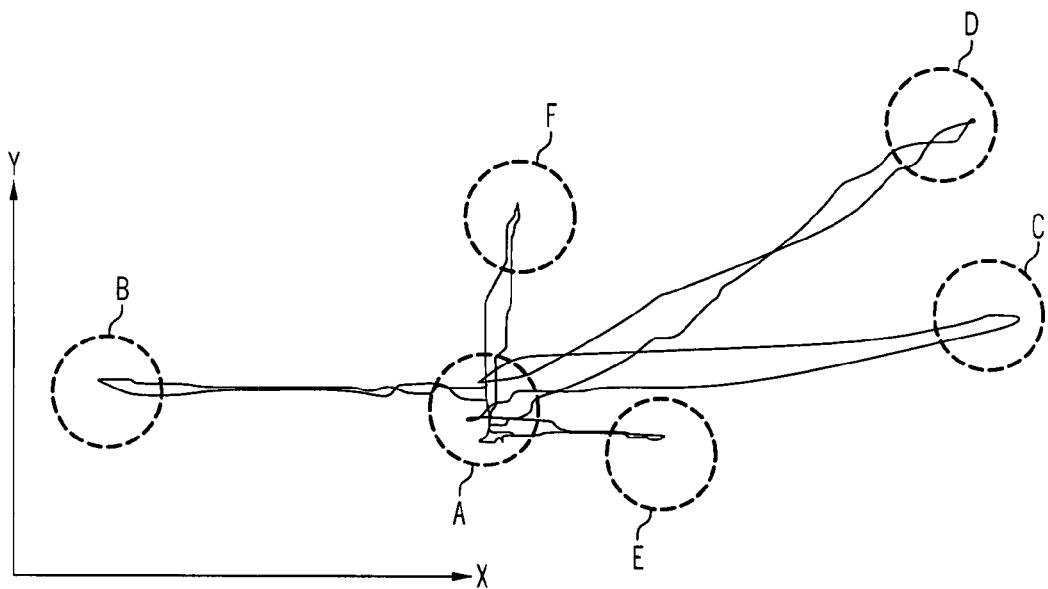
FIG. 4 graphically depicts the sensed variation in head pose of a driver over a period of vehicle operation.

The movements depicted in FIGS. 3A-3C can be integrated or summed to compute a running measure of the driver's head position or pose, provided that the driver's initial head pose is known. The trace depicted in FIG. 4 represents the computed head position over time for various common driver head movements, taking into account both the X and Y coordinates produced by the relative motion optical sensor. During forward-looking operation, the head pose tends to fall in the region designated by the letter A. The head pose temporarily moves: (1) to the region B when the driver momentarily glances at the left outside mirror, (2) to the region C when the driver momentarily glances at the right outside mirror, (3) to the region D when the driver momentarily glances at the inside rearview mirror, (4) to the region E when the driver momentarily glances at a radio display, and (5) to the region F when the driver's head momentarily tilts backward against the headrest 12. Thus, it is clearly possible to use the optical sensor apparatus 14 to determine the gaze of the driver with some accuracy, provided the initial head pose is known or can be accurately inferred. In the illustrated mechanization, however, the primary intent is to simply assess whether the driver's head pose is forward (undistracted) or non-forward (distracted).

Figure 5:
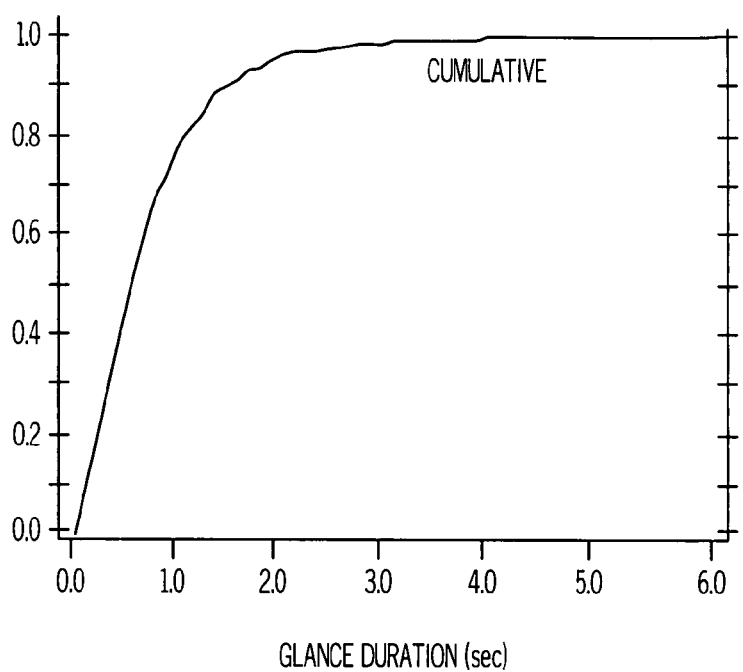
FIG. 5 graphically depicts the duration of non-forward glances by a driver instructed to look away from the forward direction as long as possible during vehicle operation.

The present invention recognizes that the head pose of a driver during vehicle operation can be inferred based on sensed head pose characteristics that are common to virtually all drivers during vehicle operation. For example, the head pose of a driver that is operating a vehicle is predominantly forward-looking, and it can be inferred that the head pose is substantially forward-looking when there is a prolonged absence of driver head movement. Furthermore, empirical data reveals that when a driver glances away from the forward direction, the duration of the glance is usually less than two seconds, and almost never more than four seconds. FIG. 5 depicts "glance-away" data for drivers who are instructed to glance away from the forward direction as long as possible while driving. The trace represents the cumulative fraction of the total glance away time. As indicated, almost 95% of the non-forward glances have a duration of no more than two seconds, even when the driver is instructed to look away as long as possible. Consequently, the driver's head pose can be periodically inferred as forward-looking based on sensed head pose movement because relatively long duration periods of little or no movement are only characteristic of the forward-looking head pose.

Figure 6:
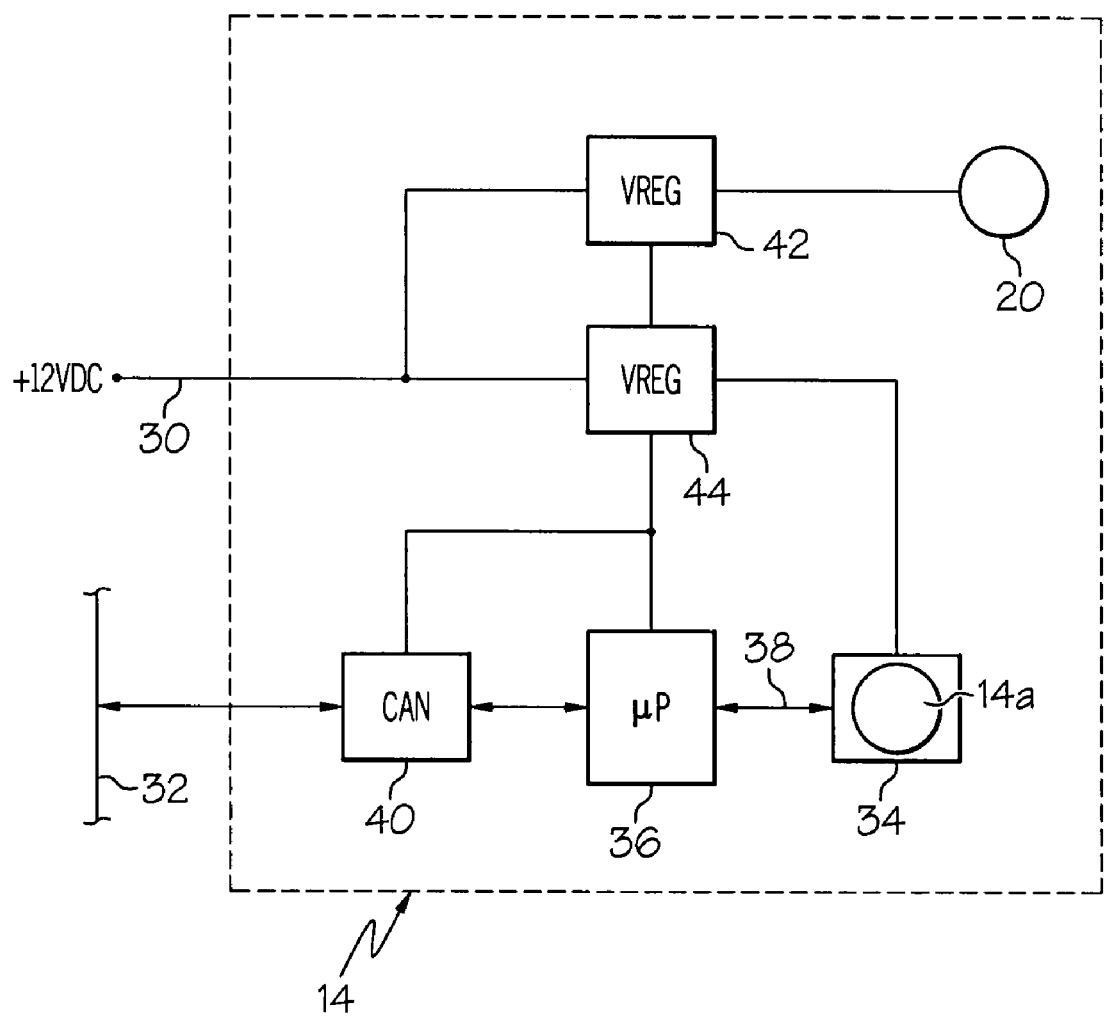
FIG. 6 is a system block diagram of an optical head pose sensing system according to the present invention, including a relative motion optical sensor and a programmed microprocessor for processing lateral output signals produced by the relative motion optical sensor.
Figure 7:
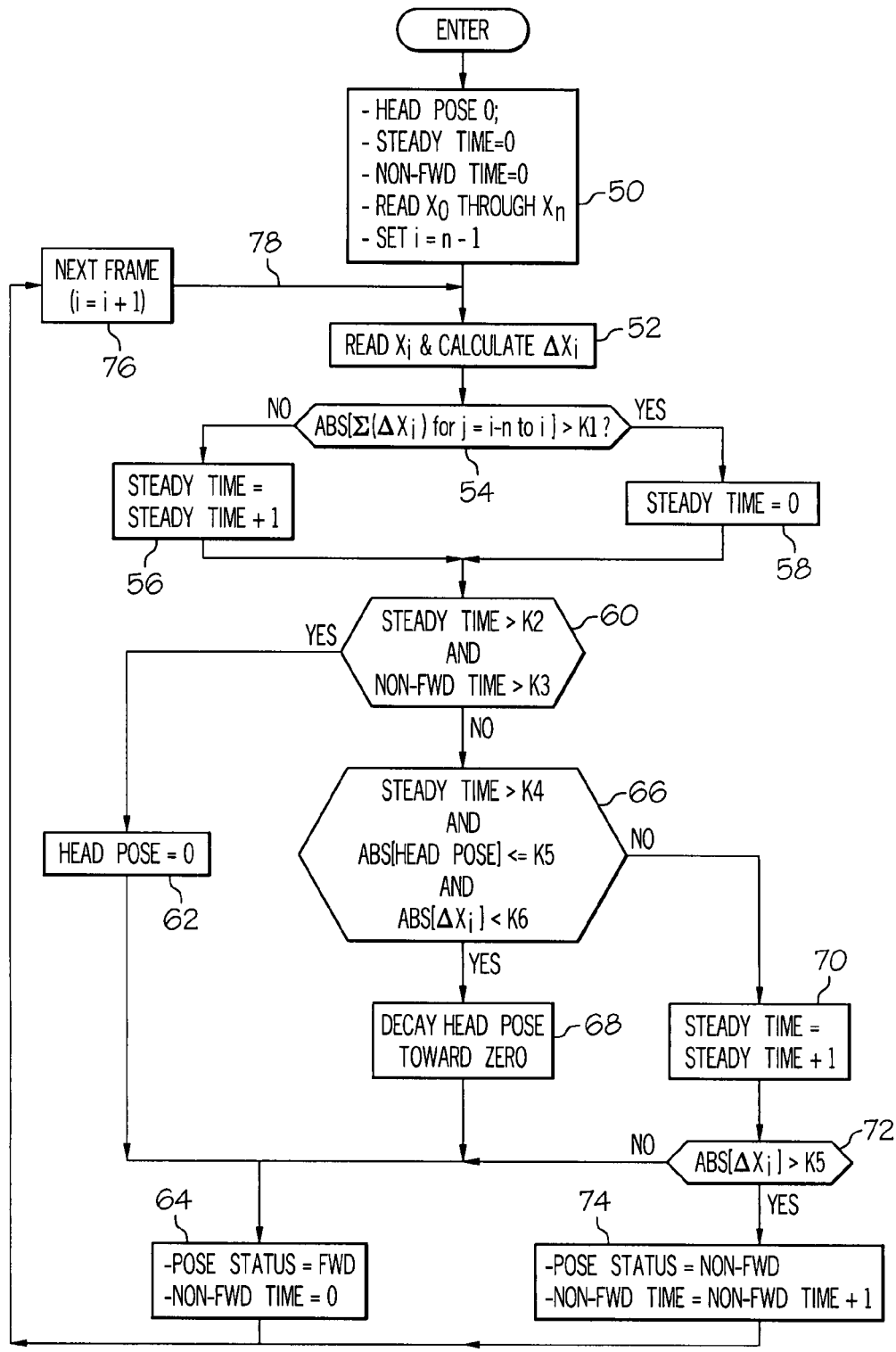
FIG. 7 is a flow diagram representing a signal processing method carried out by the microprocessor of FIG. 6 according to this invention.

FIGS. 6-7 depict a system for implementing a signal processing method for assessing the head pose of a driver based on sensed relative lateral movement using the aforementioned head movement characteristics to provide a reference for the sensed relative movements. Referring to FIG. 6, a vehicle power cable 30 supplies 12 VDC to the sensor apparatus 14, and the sensor apparatus 14 communicates with other electronic modules of the vehicle over a vehicle communications bus 32. Reference numeral 34 designates a relative motion optical sensor such as the Model No. 3080 optical mouse sensor produced and sold by Agilent Technologies, Inc., and reference numeral 36 designates an automotive-grade microprocessor (µP) or digital signal processor. Cartesian coordinate data produced by optical sensor 34 is supplied to an input port of microprocessor 36 via serial peripheral interface (SPI) 38, and microprocessor 36 communicates with the vehicle bus 32 via CAN transceiver 40. A 9V power supply 42 provides operating power to the IR LED illuminators 20, and a 3V power supply 44 provides operating power to optical sensor 34, microprocessor 36 and transceiver 40. Microprocessor 36 processes the lateral coordinate data produced by optical sensor 34 to assess the driver's head pose status; the head pose status data is supplied to other electronic modules of the vehicle via transceiver 40 and communications bus 32. For example, the head pose status data can be used to issue a driver alert in the case of an inattentive driver or to belay collision-avoidance warnings in the case of an attentive driver.

The flow diagram of FIG. 7 represents a software routine resident in and executed by microprocessor 36 for assessing whether the driver's head pose is forward or non-forward, and setting the setting the value of an output parameter (POSE_STATUS) accordingly.

Referring to FIG. 7, the block 50 designates a series of initialization instructions executed at the onset of each period of vehicle operation for resetting a number of parameters to zero and reading an initial series of lateral head pose coordinates produced by optical sensor 34. The parameters reset to zero include the apparent head pose direction HEAD_POSE, a first timer variable STEADY_TIME representing the number of successive sensor frames for which there has been no substantial head movement, and a second timer variable NON-FWD_TIME representing the number of successive sensor frames for which the POSE_STATUS is non-forward. In the case of HEAD_POSE, a zero value indicates a head pose in which the driver's concentration is focused on the forward center field-of-view. The initial lateral head pose coordinates are designated as $X_0$ through $X_n$, where n is an integer having a value of four, for example. A frame index variable i for identifying subsequently acquired lateral coordinate data is initialized to a value of (n+1).

Following initialization, the block 52 reads the lateral head pose coordinate for sensor frame i (that is, $X_i$) and determines the change in value from the previous frame (that is, $X_i - X_{i-1}$, or $\Delta X_i$). The term $\Delta X_i$ thus represents the lateral head movement between the current and previous frames of optical sensor 34. Block 54 sums the head movements over a series of (n+1) frames and compares the absolute value of the sum to a calibrated threshold K1 such as 10. If the absolute value of the sum is less than or equal to K1, the driver head pose is considered to be steady, and the timer variable STEADY_TIME is incremented by block 56. If the absolute value of the sum exceeds K1, there is significant driver head movement, and block 58 resets STEADY_TIME to zero.

Block 60 tests for a condition where there is little or no head movement and POSE_STATUS has been non-forward (NON-FWD) for a prolonged interval. Specifically, block 60 determines if: (1) STEADY_TIME exceeds a calibrated number K2 of sensor frames corresponding to two seconds, for example; and (2) NON-FWD_TIME exceeds a calibrated number K3 of frames corresponding to three seconds, for example. In other words, the condition is detected when the apparent head pose direction has been non-forward for an unreasonably long interval (based on the data discussed above in reference to FIG. 5), and there is also generally steady head movement that is characteristic of a forward-looking head pose. When this condition is detected, the routine concludes that the driver's head pose is in fact forward-looking, and blocks 62 and 64 are executed to reset both HEAD_POSE and NON-FWD_TIME to zero, and to set POSE_STATUS to FWD.

If the condition tested by block 60 is not present, the block 66 tests for a condition where there is little or no current head movement and the apparent head pose direction is generally forward-looking. Specifically, block 66 determines if: (1) STEADY_TIME exceeds a calibrated number K2 of frames corresponding to one-third second, for example; (2) ABS [HEAD_POSE] is less than or equal to a calibrated displacement K5 from forward (corresponding to a head pose angle of ±20°, for example); and (3) ABS[$\Delta X_i$] is less than a calibrated small head movement K6. When this condition is detected, the routine concludes that the driver's head pose is generally forward-looking, and blocks 68 and 64 are executed to decay the apparent head pose direction HEAD_POSE toward zero, to set POSE_STATUS to FWD, and to reset NON-FWD_TIME to zero. The term HEAD_POSE can be decayed, for example, by decrementing positive values of HEAD_POSE and incrementing negative values of HEAD_POSE.

If neither of the conditions tested by blocks 60 and 66 are present, the blocks 70 and 72 are executed to update the apparent head pose direction HEAD_POSE based on the value of $\Delta X_i$ determined at block 52, and to compare the updated HEAD_POSE to the calibrated reference value K5. As mentioned above, the reference value K5 can represent a specified head angle rotation from forward (±20°, for example). If HEAD_POSE is less than or equal to K5, the apparent head pose direction is generally forward-looking, and block 64 is executed to set POSE_STATUS to FWD and to reset NON-FWD_TIME to zero. On the other hand, if HEAD_POSE is greater than K5, the apparent head pose direction is considered to be non-forward-looking, and block 74 is executed to set POSE_STATUS to NON-FWD and to increment the timer variable NON-FWD_TIME.

Each time blocks 64 or 74 are executed to update POSE_STATUS, the routine waits for the coordinate data corresponding to the next frame of optical sensor 34 as indicated at block 76, and then repeats the execution of blocks 52-74 as indicated by flow diagram line 78. Block 76 also updates the frame index variable i for the next frame.

In the manner described above, the routine of FIG. 7 compensates for the inability of relative motion optical sensor 34 to detect the initial pose of the driver's head by returning the apparent head pose direction to (or toward) forward-looking whenever the sensed head pose behavior is indicative of a forward pose based on characteristic driver behavior during vehicle operation. And it has been demonstrated that when this method is used, the term HEAD_POSE tracks the absolute head pose position with reasonably good fidelity during vehicle operation, and the status output POSE_STATUS provides a reliable indicator of the driver's attention or inattention to the forward field-of-view.

In summary, the relative motion optical sensor 34 acquires sufficient information for reliable assessment of a driver's head pose during vehicle operation when mounted on the driver's seat rearward of the driver's head. The inability of sensor 34 to detect an initial or absolute pose of the driver's head is overcome by a signal processing method that determines the apparent head pose by integrating the sensed changes in head movement, and drives the apparent head pose toward the forward direction whenever driver behavior characteristic of a forward-looking head pose is recognized.

While the present invention has been described with respect to the illustrated embodiment, it is recognized that numerous modifications and variations in addition to those mentioned herein will occur to those skilled in the art. For example, the sensing apparatus 14 may be mounted in a location other than shown, a non-optical relative motion sensor may be used in place of the optical sensor 34, the processing routine of FIG. 7 may be configured differently than depicted, and so on. Accordingly, it is intended that the invention not be limited to the disclosed embodiment, but that it have the full scope permitted by the language of the following claims.

The invention claimed is:

1. A method of assessing a head pose of a vehicle driver, comprising the steps of:
   measuring relative lateral movements of a head of the vehicle driver with a relative position sensor responsive to a posterior portion of the head;
   acquiring the measured relative lateral movements from the relative position sensor with a signal processor;
   processing the measured relative lateral movements with the signal processor to infer an apparent direction of said head pose by tracking the relative lateral movements and identifying lateral head movement behavior characteristic of a forward head pose, and to produce an output indicating whether said apparent direction is forward or non-forward with respect to a vehicle frame of reference;
   adjusting said apparent direction toward a forward-looking direction when lateral head movement behavior characteristic of said forward head pose is identified; and summing the measured relative lateral movements over a specified interval; and identifying lateral head movement behavior characteristic of said forward head pose when the summed movements are less than a calibrated threshold for at least a predetermined time.

2. The method of claim 1, including the step of:

resetting the apparent direction of the head pose to the forward-looking direction when lateral head movement behavior characteristic of said forward head pose is identified and the assessed head pose is non-forward.

3. The method of claim 1, including the step of:

decaying the apparent direction of the head pose toward the forward-looking direction when lateral head movement behavior characteristic of said forward head pose is identified and the assessed head pose is forward.

* * * * *